United States Patent [19]
Bonadeo et al.

[11] Patent Number: 6,149,938
[45] Date of Patent: Nov. 21, 2000

[54] PROCESS FOR THE PREPARATION OF A GRANULATE SUITABLE TO THE PREPARATION OF RAPIDLY DISINTEGRABLE MOUTH-SOLUBLE TABLETS AND COMPOSITIONS OBTAINED THEREBY

[75] Inventors: Daniele Bonadeo, Varese, Italy; Franco Ciccarello, Via la Loggia Mezzovico, Switzerland; Aberto Pagano, L'Aquila, Italy

[73] Assignee: Elan Pharma International Limited, Dublin, Ireland

[21] Appl. No.: 09/122,037

[22] Filed: Jul. 23, 1998

[30] Foreign Application Priority Data

Jul. 25, 1997 [CH] Switzerland ............... 1797/97

[51] Int. Cl.[7] ............... A61K 9/20; A61K 9/16; A61K 9/50
[52] U.S. Cl. ............... 424/464; 424/497; 424/499
[58] Field of Search ............... 514/951; 424/464, 424/466, 497, 499; 427/213

[56] References Cited

U.S. PATENT DOCUMENTS

| | | | |
|---|---|---|---|
| 4,496,684 | 1/1985 | O'Connor et al. | 524/591 |
| 4,616,047 | 10/1986 | Lafon | 523/105 |
| 4,642,903 | 2/1987 | Davies | 34/5 |
| 4,851,226 | 7/1989 | Julian et al. . | |
| 5,178,878 | 1/1993 | Wehling et al. | 424/466 |
| 5,188,825 | 2/1993 | Iles et al. | 424/78.1 |
| 5,211,957 | 5/1993 | Hagemann et al. | 424/466 |
| 5,223,624 | 6/1993 | Babler et al. | 546/49 |
| 5,343,672 | 9/1994 | Kearney et al. | 53/440 |
| 5,424,074 | 6/1995 | Koli et al. | 424/464 |
| 5,457,895 | 10/1995 | Thompson et al. | 34/296 |
| 5,501,861 | 3/1996 | Makino et al. | 424/464 |
| 5,570,143 | 10/1996 | Newman | 351/176 |
| 5,607,697 | 3/1997 | Alkire et al. . | |
| 5,631,023 | 5/1997 | Kearney et al. | 424/465 |
| 5,720,974 | 2/1998 | Makino et al. | 424/464 |
| 5,792,958 | 8/1998 | Speldrich | 73/727 |

*Primary Examiner*—Thurman K. Page
*Assistant Examiner*—Alysia Berman
*Attorney, Agent, or Firm*—Kirsten A. Anderson

[57] ABSTRACT

A process for making a granulate composition suitable to the preparation of an oral solid form that can disintegrate rapidly inside the buccal cavity is provided as well as the granulate compositions and obtained.

8 Claims, No Drawings

PROCESS FOR THE PREPARATION OF A GRANULATE SUITABLE TO THE PREPARATION OF RAPIDLY DISINTEGRABLE MOUTH-SOLUBLE TABLETS AND COMPOSITIONS OBTAINED THEREBY

RELATED APPLICATIONS

This patent application is related to Swiss Patent Application 1797/97 filed Jul. 25, 1997, (abandoned) under 35 U.S.C. §119.

FIELD OF THE INVENTION

The invention relates to a process for the preparation of a granulate used in making rapidly disintegrable mouth-soluble tablets.

TECHNOLOGICAL BACKGROUND

One of the changes occurring in modern society is the progressive ageing of population. Such a phenomenon is accompanied by the onset of degenerative pathologies involving difficulties in coordination and in swallowing the traditional oral forms such as tablets or capsules. Said problems are also present, in other population groups, such as children.

On the other hand, the need for solid pharmaceutical forms capable of making the medicament available within a short time from the administration is particularly felt even for those patients who do not have any swallowing problems.

In some fields of therapy, such as that relating analgesia, fast acting medicaments to be administered by the oral route are nowadays particularly required.

The conventional solution to such a problem is usually provided by water-soluble effervescent tablets.

In this case, the patient ingests the aqueous solution resulting from the disintegration of the tablet in water so that the active ingredient already dissolved or dispersed in water is in a highly bio-available form.

A number of methods for the preparation of granulates suitable to the preparation of effervescent tablets are known. One of said methods, so-called "single phase", consists in keeping in suspension, in an air stream, the effervescent mixture and optionally any excipients and in granulating said mixture using water and/or a binding polymer. The mass, after the granulation phase, is dried, sieved and collected in a single operation.

The effervescent tablets, however, in order to be administered, have to be dispersed in a carrier, since they cannot be ingested directly. This is in many cases, a restriction to the use of such a pharmaceutical formulation for the above mentioned population groups.

Therefore, tablets that dissolve in the mouth, that are to the oral or sublingual administration, have been suggested.

The buccal tablets are intended for disintegration in the mouth, the patient placing them in the buccal cavity, on the tongue or between cheeks and gums, thereby allowing a slow dissolution, which usually requires 30 to 60 minutes (E. Rotteglia "Compresse farmaceutiche", Societa Editoriale Farmaceutica, Milan, Italy, 1966).

On the contrary, sublingual tablets are intended to be placed under the tongue, wherein the active substance can be directly absorbed through the mucosa. These forms are provided with slow-disintegration formulations as well (E. Rotteglia, ibid. and S. Casadio, Tecnologia Farmaceutica II Ed., Cisalpina Goliardica, Milan, Italy).

This type of prolonged release is hardly suitable for formulating active ingredients, such as analgesics, which have to exert an immediate effect.

Such a requirement can be met by freeze-dried sublingual tablets such as those prepared according to the Zydis patented (R) procedure for creating a rapidly dissolving oral formulation. Zydis is a registered trademark of the R.P. Scherer Company (Manufacturing Chemist, 36–37, February 1990).

However, such formulations are very expensive and require sophisticated technologies and methods from the production point of view. These products are substantially freeze-dried products, the pharmaceutical formulation being therefore difficult to handle (due to its high friability and fragility) and requiring specific packaging. A problem with freeze-dried sublingual tablet formulations is the impossibility to effect any taste-masking on the active ingredient.

WO 8808298 (Fuisz Technologies, Nov. 3, 1988) discloses rapid-dissolution pharmaceutical compositions in which the active ingredient is included in a water-soluble carrier obtained through a specific preparation process which requires a specific, expensive plant. Moreover, the resulting compositions exhibit friability problems and must always be handled and packed with particular precautions (use of dehydrating agents, humidity-tight packages, controlled-humidity work environment and so on).

EP-A-494972 (Cima Labs Inc.; Jul. 22, 1992) describes effervescent tablets suitable to the direct oral administration, i.e. without a previous development of the effervescence in water, consisting of microcapsules containing the active ingredients and an amount of effervescent agents sufficient to promote the release of the microgranules when ingested and to give a "fizzing" sensation when in contact with the buccal mucosa of the patient.

The amount of effervescent agents, typically citric acid and a carbonate or a bicarbonate, ranges from 5 to 50% by weight compared with the composition total weight, preferably from 15 to 30%. Dissolution times in the mouth range from 30 seconds to 5–7 minutes.

In this case also, notwithstanding the presence of amounts of effervescent agents lower than in conventional formulations (60% by weight compared with the composition total), the typical cautions used for the effervescent tablets should be taken.

Further drawbacks are the friability of the tablets and the use of microcapsules. In fact, the preparation technique described in EP-A-494972 does not envisage the humid granulation, i.e. using a solvent, but the direct mixing of the powders and the subsequent compression. Such a preparation technique yields tablets having friability values higher than those involving the humid granulation of the mixture to be pressed.

SUMMARY OF THE INVENTION

Now it has been found that mouth-soluble, rapidly disintegrating tablets can be prepared by fluidized bed granulating an aqueous solution of a water-soluble or water-dispersible polymer in a polyalcohol, optionally in mixture with other solid components.

The granulate obtained according to the invention, characterized by a high porosity and a low apparent density, allows the preparation of tablets rapidly disintegrating in contact with saliva in times ranging, for example, from 30" to 3', even without the aid of effervescent agents.

If desired, however, the effervescent agents can be present in the granulate composition in order to promote further the disintegration of the tablets. For this purpose, markedly lower amounts of effervescent agents than those usually employed in the conventional effervescent compositions may be used. About 20% by weight of effervescent agents on the basis of the total tablet assures for example an exceedingly rapid dissolution, but even lower amounts, for example lower than 5%, provide similar disintegration times.

Moreover, it has surprisingly been found that substantially the same disintegrating effect can also be obtained using the only acid component of the effervescent couple.

The compositions obtainable according to the invention, in addition to disintegration times lower or anyhow comparable to those of the traditional effervescent formulations, have the following further advantages:
high stability;
very good organoleptic characteristics;
handling and packaging without need for the cautions and measures required for the effervescent formulations.

DETAILED DISCLOSURE OF THE INVENTION

The method according to the invention consists in the fluidized bed granulation in a water-soluble or water-dispersible polymer, a diluent of the class of polyalcohols and optionally other solid components such as active ingredients, flavors, sweetening agents, surfactants, disintegration agents.

The polyalcohols which can be used according to the invention are those usable for alimentary purposes and are preferably selected from mannitol, xylitol, sorbitol, maltitol, erythritol and lactitol. Particularly preferred are sorbitol or xylitol which have high water-solubility, a negative heat of dissolution, capable of giving a pleasant feeling of freshness. The polyalcohol will be from about 50 to about 90% of the total weight of the tablet obtained by compression of the granulate.

Water-soluble or water-dispersible polymers are selected from those conventionally used in the pharmaceutical field. Examples of said polymers comprise polyethylene glycols, sodium carboxymethyl cellulose, hydroxypropylmethyl cellulose, xanthan gum, polyethylene oxide (Polyox® ), ethoxylated polyoxypropylene (Pluronic®), acrylic and methacrylic acid polymers (Eudragit®), carrageenin, ethyl cellulose (Acquacoat®), polyvinyl alcohol. The amount of the polymer dissolved or dispersed in water varies from 1 to 10% by weight of the total composition.

The fluidized bed granulation is usually carried out adjusting the operative conditions, so that the temperature of the inlet air is from 30 to 50° C. and the temperature of the outlet air is from 25 to 45° C. The flow of the distributed solution will depend of course on the size and type of the plant. In principle, for a pilot plant of the type Niro Aereomatic Strea 1 flows ranging between 10 and 15 ml/min of polymer solution or dispersion will be used.

In addition to the polyalcohol, the solid phase can contain all or some of the other components (active ingredient, flavors, sweeteners, and the like) that can be mixed with the granulate before compression. Such an alternative can be suitable for highly thermo-sensitive components or excipients such as lubricants, flavours, disintegrating agents.

When present, the effervescent mixture can consist of acids and bases for alimentary use.

The acid source can consist of citric, tartaric, malic, fumaric, adipic, succinic, alginic acids, anhydrides and acid salts such as dihydrogen phosphate, disodium dihydrogen phosphate, citric acid salts.

The bases can be: solid carbonates of salts such as sodium carbonate, sodium bicarbonate, potassium bicarbonate, potassium carbonate, magnesium carbonate, sodium glycine carbonate, L-lysine carbonate, arginine carbonate and amorphous calcium.

The amount of effervescent mixture or of the acid only is preferably lower than 20% by weight of the total composition, most preferably lower than 5%.

Alternatively, the compositions of the invention can contain only the acid component, particularly citric acid, in weight percentages from 1 to 4% of the total.

The compositions obtainable according to the process of the invention are suitable for the administration of any active ingredient which can be administered orally and capable of being absorbed by the buccal mucosa and/or by the gastrointestinal tract. If desired, the active ingredients may be previously coated.

Moreover, the compositions obtainable according to the process of the invention are particularly suitable for the administration of vitamins, mineral salts, dietary supplements, vegetable extracts and mixtures thereof.

Examples of active ingredients which can be used in the process of the invention comprise: antitussives, anthistamines, decongestants, antacids, analgesics, antiinflammatories, antibiotics, anticholesterol agents, antiarrhythmics, antiepileptics, anorexizants, expextorants, antianxiety agents, antiulcer drugs, coronary dilators, psychotropics, antipsychotics, antineoplastics, antiemetics, hypnotics, antikynetosic agents, muscle relaxants, neuromuscular agents, hypoglycemic agents, hyperglycemic agents, thyroid suppressors and stimulants, diuretics, antispasmodics, uterine relaxants, anabolic agents and combinations thereof.

Examples of vitamins comprise Vitamin C, Vitamin E, Vitamin D, Vitamin K, Vitamin A, Vitamin B complex, folic acid, choline, carnitine, carnosine, carotenoids, lycopene, optionally in the form of coenzymes.

Examples of mineral salts comprise salts of essential elements such as calcium, magnesium, iron, zinc, selenium, copper, iodine, phosphorous, chromium, cobalt, manganese, optionally in mixtures thereof.

Examples of dietary supplements comprise amino- acids, proteins, vegetable or fish oils, ginseng, bran, honey, royal jelly, meals and the like.

Examples of derivatives or extracts of natural origin comprise green tea, Ginseng, Guarany, Ginkgo biloba, bilberry extracts, proanthocyanosides, grape-seed extracts and the like.

The flavor, which is an important feature of this type of pharmaceutical formulations, can be included in the outer phase during the final mixing with other excipients or, making use of the fluidized bed granulation technique, it can be sprayed on the granulate and then on the active ingredient, exploiting in some cases the capability of tastemasking of the flavor on the active ingredient.

The flavors can be selected from synthetic or natural flavors, extracts from plants or flowers, alone or in a combination with, essential oils such as cinnamon, peppermint, clove, anise, eucalyptus, thyme, cedar, or chamomile oils. Other flavors useful are fruits essences such as apple, peach, strawberry, raspberry, orange, apricot, cherry, plum, pineapple, bubble gum alone or in a combination thereof.

The amount of flavor used can vary, depending on a number of factors such as the intensity of the desired organoleptic effect: the amount can anyhow vary from 0.5 to 3.0% on the basis of the composition total weight.

The compositions of the invention can moreover contain disintegration agents such as microcrystalline cellulose coated with arabic gum; potato or maize starches, modified starches, polyvinylpyrrolidone, cross-povidone, alginic acid, starch sodium glycolate, agar, in amount ranging from 2 to 10% on the basis of the composition total weight.

The compositions can optionally contain coloring agents such as titanium dioxide, acceptable natural or synthetic coloring agents, which can be sprayed during the granulation phase.

The lubricants and surfactants can be added to the granulate both during the final mixing phase before compression and during the granulation.

Among the traditional solid lubricants, Ca, Mg, Zn of stearic acid salts, partially hydrogenated vegetable oils, polyethylene glycols, polyoxyethylene monostearate, talc, sodium benzoate, sodium laurylsulfate, magnesium oxide can be used.

The amount of lubricant to be added can vary from 0.2% to 1.0% of the total composition.

In all of the excipient mixtures, the poured apparent density before and after the granulation has been evaluated.

Before the granulation, the density varies from 0.6 to 0.8 g/ml, after the granulation process in the conditions defined above the density decreases to 0.3 - 0.5 g/ml.

These data confirm the capability of this method of producing low-density, and therefore high-porosity, granulates.

This porous structure is maintained even after compression of the granulate, thereby obtaining tablets with a variable hardness of 6–7 Kp which disintegrate in a time ranging between 30" and 120".

In order to increase the disintegration rate, the granulate obtained according to the invention can be compressed to a form so as to increase the tablet surface, for example in a circular form with a substantially toroidal section, as shown in FIG. 1a (plant view) and in FIG. 1b (sectional view)

The following examples illustrate the invention in greater detail.

EXAMPLE 1

Nimesulide mouth-soluble tablets (100 mg of Nimesulide for 1.0 g tablet, diameter 16 mm)

|   | Amount × 1000 mg | Amount batch 500 g (500 tbl) |
|---|---|---|
| 1 Nimesulide | 100.0 mg | 50.0 g |
| 2 Citric acid crystals | 19.0 mg | 9.5 g |
| 3 Sodium bicarbonate | 19.0 mg | 9.5 g |
| 4 Sorbitol | 820.0 mg | 410.0 g |
| 5 Aspartame | 4.0 mg | 2.0 g |
| 6 PEG 6000 | 20.0 mg | 10.0 g |
| 7 Strawberry flavor | 15.0 mg | 7.5 g |
| 8 Magnesium stearate | 3.0 mg | 1.5 g |
| TOTAL | 1000.0 mg | 500.0 g |

Preparation method

The components 1, 2, 3, 4 and 5, previously weighed and sieved, were transferred to a fluidized bed (Niro Aeromatic Strea 1). The granulation was carried out with a PEG 6000 aqueous solution in 50 ml of water with a 10 ml/minute flow (peristaltic pump) and with inlet air temperature of 40° C.

The resulting granulate, after drying, cooling and sieving, was mixed with the components 7 and 8.

The mixture obtained was tabletted with a 16 mm diameter punch.

EXAMPLE 2

Nimesulide mouth-soluble tablets (100 mg of Nimesulide per 1.0 g tablet, diameter 16 mm)

|   | Amount × 1000 mg tbl | Amount per batch 500 g tbl (500 tbl) |
|---|---|---|
| 1 Nimesulide | 100.0 mg | 50.0 g |
| 2 Citric acid crystals | 38.0 mg | 19.0 g |
| 3 Sorbitol | 820.0 mg | 410.0 g |
| 4 Aspartame | 4.0 mg | 2.0 g |
| 5 PEG 6000 | 20.0 mg | 10.0 g |
| 6 Strawberry flavor | 15.0 mg | 7.5 g |
| 7 Magnesium stearate | 3.0 mg | 1.5 g |
| TOTAL | 1000,0 mg | 500.0 g |

Preparation method

The components 1, 2, 3 and 4, previously weighed and sieved, were transferred to a fluidized bed (Niro Aeromatic Strea 1). The granulation was carried out with a PEG 6000 aqueous solution in 50 ml of water with a 10 ml/minute flow (peristaltic pump) and with inlet air temperature of 50° C.

The resulting granulate, after drying, cooling and sieving, was mixed with the components 6 and 7.

The mixture obtained was tabletted with a 16 mm diameter punch.

EXAMPLE 3

Mouth-soluble multi-vitamin tablet (1.0 g tablets, diameter 16 mm)

|   | Amount × 1000 mg tbl | Amount × batch 600 g tbl (600 tbl) |
|---|---|---|
| 1 Vitamin $B_{12}$ 0.1% | 1.4 mg | 0.840 g |
| 2 Vitamin $B_2$ 5 phosph. Na 2 $H_2O$ | 1.9 mg | 1.140 g |
| 3 Vitamin A palmitate 250 cws | 8.33 mg | 4.988 g |
| 4 Vitamin $B_1$ mononitrate | 1.10 mg | 0.660 g |
| 5 Vitamin $B_6$ HCl | 1.61 mg | 0.966 g |
| 6 Vitamin C | 56.25 mg | 33.750 g |
| 7 Vitamin $D_3$ 100 cws | 5.0 mg | 3.000 g |
| 8 Vitamin E 50% acetate | 23.99 mg | 14.394 g |
| 9 Folic acid | 0.134 mg | 0.081 g |
| 10 Biotin | 0.036 mg | 0.021 g |
| 11 Vitamin PP 33 ⅓ rocoat | 42.90 mg | 25.740 g |
| 12 Carotene (tab 10% And) | 15.0 mg | 9.000 g |
| 13 Sorbitol | 761.35 mg | 456.810 g |
| 14 Citric acid | 38.0 mg | 22.800 g |
| 15 Aspartame | 5.0 mg | 3.000 g |
| 16 PEG 6000 | 20.0 mg | 12.000 g |

-continued

|  | Amount × 1000 mg tbl | Amount × batch 600 g tbl (600 tbl) |
|---|---|---|
| 17 Orange flavor | 15.0 mg | 9.000 g |
| 18 Magnesium stearate | 3.0 mg | 1.800 g |
| TOTAL | 1000,0 mg | 600.000 g |

Preparation method

The components 1, 2, 3, 4, 5, 6, 7, 8, 9, 10, 13 and 15, previously weighed and sieved, were transferred to a fluidized bed (Niro Aeromatic Strea 1). The granulation was carried out with a PEG 6000 aqueous solution in 60 ml of water with a 8 ml/minute flow (peristaltic pump) and with inlet air temperature of 35° C.

The resulting granulate, after drying, cooling and sieving, was mixed with the remaining components.

The mixture obtained was tabletted with a 16 mm diameter punch.

EXAMPLE 4

Acetylsalicylic acid mouth-soluble tablets (300 mg of acetylsalicylic acid for 1.1 g tablet, diameter 16 mm)

|  | Am. × tbl 1100 mg | Am. × a batch 220 g (200 tbl) |
|---|---|---|
| 1 Sorbitol | 745 mg | 149.0 g |
| 2 Aspartam | 4.0 mg | 0.8 g |
| 3 PEG 6000 | 20.0 mg | 4.0 g |
| 4 Acetylsalicylic acid | 300.0 mg | 60.0 g |
| 5 Strawberry flavor | 25.0 mg | 5.0 g |
| 6 Magnesium stearate | 6.0 mg | 1.2 g |
| TOTAL | 1100.0 mg | 220 g |

Preparation method

The components 1 and 2, previously weighed and sieved, were transferred to a fluidized bed (Niro Aeromatic Strea 1). The granulation was carried out with a PEG 6000 aqueous solution in 50 ml of water with a 10 ml/minute flow (peristaltic pump) and with inlet air temperature of 45° C.

The resulting granulate, after drying, cooling and sieving, was mixed with the components 4, 5 and 6.

The mixture obtained was tabletted with a 16 mm diameter punch.

EXAMPLE 5

Paracetamol (Pharmazome I.R.) mouth-soluble tablets (500 mg of paracetamol for 2.0 g tablet, diameter 19 mm)

|  | Am. × tbl 2000 mg | Am. × a batch 500 g (500 tbl) |
|---|---|---|
| 1 Paracetamol Ph.z. I.R. | 750.0 mg | 225.0 g |
| 2 Mannitol | 280.0 mg | 84.0 g |
| 3 Xylitol | 841.0 mg | 525.3 g |
| 4 Citric acid crystals | 40.0 mg | 12.0 g |
| 5 Sodium bicarbonate | 40.0 mg | 12.0 g |
| 6 Aspartame | 4.0 mg | 1.2 g |
| 7 PEG 6000 | 20.0 mg | 6.0 g |

-continued

|  | Am. × tbl 2000 mg | Am. × a batch 500 g (500 tbl) |
|---|---|---|
| 8 Orange flavor | 20.0 mg | 6.0 g |
| 9 Magnesium stearate | 5.0 mg | 1.5 g |
| TOTAL | 2000.0 mg | 600.0 g |

Preparation method

The components 1, 2, 3, 4, 5 and 6, previously weighed and sieved, were transferred to a fluidized bed (Niro Aeromatic Strea 1). The granulation was carried out with a PEG 6000 aqueous solution in 60 ml of water with a 10 ml/minute flow (peristaltic pump) and with inlet air temperature of 50° C.

The resulting granulate, after drying, cooling and sieving, was mixed with the components 8 and 9.

The mixture obtained was tabletted with a 19 mm diameter punch.

EXAMPLE 6

Green tea mouth-soluble tablets (50 mg of Green tea for 1.8 g tablet, diameter 19 mm)

|  | Am. × tbl 1500 mg | Am. × a batch 750 g (500 tbl) |
|---|---|---|
| 1 Green tea | 50.0 mg | 25.00 g |
| 2 Sorbitol | 1337.0 mg | 668.50 g |
| 3 Citric acid crystals | 40.0 mg | 20.00 g |
| 4 Sodium bicarbonate | 20.0 mg | 10.00 g |
| 5 Aspartame | 9.0 mg | 4.50 g |
| 6 PEG 6000 | 15.0 mg | 7.50 g |
| 7 Berry flavor | 25.0 mg | 12.50 g |
| 8 Magnesium stearate | 4.0 mg | 2.00 g |
| TOTAL | 1500.0 mg | 750.00 g |

Preparation method

The components 1, 2, 3, 4 and 5, previously weighed and sieved, were transferred to a fluidized bed (Niro Aeromatic Strea 1). The granulation was carried out with a PEG 6000 aqueous solution in 50 ml of water with a 11.2 ml/minute flow (peristaltic pump) and with inlet air temperature of 50° C.

The resulting granulate, after drying, cooling and sieving, was mixed with the components 7 and 8.

The mixture obtained was tabletted with a 19 mm diameter punch.

EXAMPLE 7

Cimetidine mouth-soluble tablets (50 mg of Cimetidine for 1.0 g tablet, diameter 16 mm)

|  | Am. × tbl 1000 mg | Am. × a batch 700 g (700 tbl) |
|---|---|---|
| 1 Cimetidine | 50.0 mg | 35.000 g |
| 2 Xylitol | 7.5 mg | 5.250 g |
| 3 Aerosil 2000 | 3.0 mg | 2.100 g |
| 4 Monoammonium glycyrrhizinate | 0.3 mg | 0.210 g |

-continued

|  | Am. × tbl<br>1000 mg | Am. × a batch<br>700 g (700 tbl) |
|---|---|---|
| 5 Aspartame | 4.0 mg | 2.800 g |
| 6 Eudragit L30D55 | 10.0 mg | 7.000 g |
| 7 Talc | 5.08 mg | 3.556 g |
| 8 Simethicone antifoam | 0.12 mg | 0.084 g |
| 9 Triethyl citrate | 1.0 mg | 0.700 g |
| 10 Xylitol | 831.0 mg | 581.700 g |
| 11 PEG 6000 | 20.0 mg | 14.000 g |
| 12 Citric acid crystals | 19.0 mg | 13.300 g |
| 13 Sodium bicarbonate | 19.0 mg | 13.300 g |
| 14 Raspberry flavor | 25.0 mg | 17.500 g |
| 15 Magnesium stearate | 5.0 mg | 3.500 g |
| TOTAL | 1000,0 mg | 700.000 g |

Preparation method

The components 1, 2 and 3, previously weighed and sieved, were transferred to a fluidized bed. First a solution of the components 4 and 5 in 50 ml of water were sprayed with a dispersion of the components 6, 7, 8 and 9 in 20 ml of water. After drying, the components 10, 12 and 13 and were added, granulating with a solution of PEG 6000 in 60 ml of water, using a 10 ml/minute flow (peristaltic pump) and with inlet air temperature of 50° C.

The resulting granulate, after drying, cooling and sieving, was mixed with the components 14 and 15.

The mixture obtained was tabletted with a 16 mm diameter punch.

EXAMPLE 8

Ibuprofen mouth-soluble tablets (100 mg of Ibuprofen for 1.0 g tablet, diameter 16 mm)

|  | Am. × tbl<br>1000 mg | Am. × a batch<br>500 g (500 tbl) |
|---|---|---|
| 1 Ibuprofen | 100.0 mg | 50.0 g |
| 2 Xylitol | 10.0 mg | 5.0 g |
| 3 Eudragit L30D 55 | 20.0 mg | 10.0 g |
| 4 Talc | 10.6 mg | 5.3 g |
| 5 Simethicone antifoam | 0.24 mg | 0.12 g |
| 6 Triethyl citrate | 2.0 mg | 1.0 g |
| 7 Liquid flavor | 0.0001 mg | 0.00005 g |
| 8 Cremophor RH40 | 0.0001 mg | 0.00005 g |
| 9 Xylitol | 751.5598 mg | 375.7799 g |
| 10 Citric acid crystals | 50.0 mg | 25.0 g |
| 11 Aspartame | 10.0 mg | 5.0 g |
| 12 Polyoxylresin WRSN10 | 6.6 mg | 3.3 g |
| 13 Mint flavor | 5.0 mg | 2.5 g |

-continued

|  | Am. × tbl<br>1000 mg | Am. × a batch<br>500 g (500 tbl) |
|---|---|---|
| 14 Orange flavor | 30.0 mg | 15.0 g |
| 15 Magnesium stearate | 4.0 mg | 2.0 g |
| TOTAL | 1000,0 mg | 500.0 g |

Preparation method

The components 1 and 2, previously weighed and sieved, were transferred into a fluidized bed. First a solution of the components 3, 4, 5 and 6 in 11.5 ml of water were sprayed with a solution of the components 7 and 8 in 25 ml of water. After drying, the components 9, 10 and 11 were added, granulating with a solution of 12 in 50 ml of water, using a 10 ml/minute flow (peristaltic pump) and with inlet air temperature of 40° C.

The resulting granulate, after drying, cooling and sieving, was mixed with the components 13, 14 and 15.

The mixture obtained was tabletted with a 16 mm diameter punch.

EXAMPLE 9

N-Acetyl-cysteine mouth-soluble tablets (200 mg of N-Acetyl-cysteine for 1.2 g tablet, diameter 16 mm).

|  | Am. × tbl<br>1200 mg | Am. ×. a<br>Batch 600 g |
|---|---|---|
| 1 N-Acetyl-cysteine | 200 mg | 100.0 g |
| 2 Citric acid | 21.8 mg | 10.9 g |
| 3 Mannitol | 476.0 mg | 238.0 g |
| 4 Sorbitol | 221.0 mg | 110.5 g |
| 5 Polyplasdone CL | 60.0 mg | 30.0 g |
| 6 PEG 6000 | 15.0 mg | 7.5 g |
| 7 Magnesium Stearate | 8.0 mg | 4.0 g |
| 8 Aspartame | 10.0 mg | 5.0 g |
| 9 Sodium Bicarbonate | 98.2 mg | 49.1 g |
| 10 Avicel CE 15 | 60.0 mg | 30.0 g |
| 11 Lemon Flavor | 15.0 mg | 7.5 g |
| 12 Tangerine Flavor | 15.0 mg | 7.5 g |
| TOTAL | 1200 mg | 600.0 g |

Preparation Method

The components 1, 2, 3, 4 and 5, previously weighed and sieved, were transferred to a fluidized bed (Niro Aeromatic Strea 1). The granulation was carried out with a PEG 6000 aqueous solution in 50 ml of water with a 11.2 ml/minute flow (Peristaltic pump) and with inlet air temperature of 50° C.

The resulting granulate, after drying, cooling and sieving, was mixed with the components 7, 8, 9, 10, 11 and 12.

The mixture obtained was tabletted with 16 mm diameter punch.

In the following table, the results of the physical controls carried out on the preparations of Examples 1–9 are listed.

| Example n. | 1 | 2 | 3 | 4 | 5 | 6 | 7 | 8 | 9 |
|---|---|---|---|---|---|---|---|---|---|
| Powders mixture before granulation | | | | | | | | | |
| Apparent density (g/ml) | 0.74 | 0.70 | 0.60 | 0.60 | 0.72 | 0.73 | 0.68 | 0.74 | 0.75 |

-continued

| Example n. | 1 | 2 | 3 | 4 | 5 | 6 | 7 | 8 | 9 |
|---|---|---|---|---|---|---|---|---|---|
| Granulate before compression | | | | | | | | | |
| Apparent density (g/ml) | 0.50 | 0.47 | 0.40 | 0.41 | 0.50 | 0.46 | 0.50 | 0.47 | 0.50 |
| Tablets | | | | | | | | | |
| Diameter (mm) | 16 | 16 | 16 | 16 | 19 | 19 | 16 | 16 | 16 |
| Weight (g) | 1000 | 1000 | 1000 | 1100 | 2000 | 1500 | 1000 | 1000 | 1200 |
| Hardness (kp) | 7.0 | 7.4 | 7.0 | 6.0 | 7.0 | 6.0 | 6.7 | 6.2 | 7.0 |
| Disintegration time (sec.) | 125 | 30 | 120 | 30 | 100 | 140 | 100 | 60 | 60 |

What is claimed is:

1. A process for making a granulate for use in the preparation of mouth-soluble, rapidly disintegrating tablets, which process comprises:
   (i) granulating in a fluidized bed
      (a) a polyalcohol;
      (b) an active ingredient;
      (c) from 1 to 30% of an edible acid wherein the edible acid is not part of an effervescent mixture consisting of an acid and a base;
      (d) optionally, other solid components selected from the group consisting of lubricants, sweetening agents, and flavors; and
      (e) an aqueous solution or aqueous dispersion of a water-soluble or water-dispersible polymer that provides 1–10% of the final weight of the granulate; and
   (ii) drying the granulate in the fluidized bed.

2. A process according to claim 1 in which the water-soluble or water-dispersible polymers are selected from the group consisting of polyethylene glycols, sodium carboxymethyl cellulose, hydroxypropylmethyl cellulose, xanthan gum, polyethylene oxide, polyoxyethylene, polyoxypropylene Pluronic®, acrylic and methacrylic acid polymers Eudragit®, carrageenin, polyvinyl alcohol.

3. A process according to claim 1 in which the polyalcohols are selected from the group consisting of mannitol, xylitol, sorbitol, erythritol, maltitol, lactitol.

4. A process according to claim 3, in which the polyalcohols are selected from the group consisting of xylitol and sorbitol.

5. A process according to claim 4 in which the active ingredients have been coated before the granulation.

6. Mouth-soluble, rapidly disintegrating tablets comprising the granulate of claim 1.

7. Tablets according to claim 6 having a disintegration time ranging from 30 seconds to 3 minutes.

8. A process of making a mouth-soluble, rapidly disintegrating tablet comprising comprising the granulate of claim 1 and optionally, other components to form a tablet.

* * * * *